United States Patent [19]

Oertle et al.

[11] 4,145,915

[45] Mar. 27, 1979

[54] EARLY CRACK DETECTION

[75] Inventors: Donald H. Oertle; Marvin L. Peterson, both of Ponca City, Okla.

[73] Assignee: Continental Oil Company, Ponca City, Okla.

[21] Appl. No.: 890,559

[22] Filed: Mar. 20, 1978

Related U.S. Application Data

[63] Continuation of Ser. No. 778,660, Mar. 17, 1977, abandoned.

[51] Int. Cl.² .............................................. G01M 3/04
[52] U.S. Cl. ........................................................ 73/37
[58] Field of Search ........................... 73/37, 40, 104; 116/114 P; 340/240, 242

[56] References Cited

U.S. PATENT DOCUMENTS

| | | | |
|---|---|---|---|
| 2,185,315 | 1/1940 | Rogatchoff | 73/104 |
| 3,299,417 | 1/1967 | Sibthorpe | 340/242 |
| 3,820,381 | 6/1974 | Thurston | 73/40 |

Primary Examiner—S. Clement Swisher
Attorney, Agent, or Firm—A. Joe Reinert

[57] ABSTRACT

Early detection of cracks in non-permeable, structural members subject to stress is effected before the cracks traverse the member by:

(a) forming a cavity in the structural member or adjacent thereto such that a crack forming in the structural member provides a passage for a fluid to flow between the environment and the cavity without passing through the entire structural member, (b) sealing a fluid passageway in fluid communication from the cavity to a source of pressure different than ambient pressure at the structural member and to a pressure sensor, (c) imparting a higher or lower pressure to the cavity and the fluid passageway, and, (d) monitoring the internal pressure in the cavity and fluid passageway with the pressure sensor, such that a crack in the structural member penetrating to the cavity allows passage of fluid between the environment and the cavity and is thus detected by the pressure sensor. The apparatus and process is particularly applicable to early detection with vacuum of cracks in the heat affected zone adjacent to welds on critical stressed members of an offshore platform. A strain guage system may be employed in conjunction with the crack detection system.

43 Claims, 11 Drawing Figures

EARLY CRACK DETECTION

This is a continuation, of application Ser. No. 778,660 filed Mar. 17, 1977 now abandoned.

BACKGROUND OF THE INVENTION

The invention relates to early detection of the formation of cracks in non-permeable, structural members subject to stress.

In an important application the invention relates to early detection of cracks in critical stressed members of an offshore platform employed to drill for or produce oil or gas.

BRIEF DESCRIPTION OF THE PRIOR ART

Formation of cracks in solid structural members subject to stress is a problem of great importance. In one example, offshore production and drilling platforms are an important aspect of fulfilling the energy needs of the nation and the world. Such platforms are being fabricated to drill and produce in deeper and deeper waters. To illustrate, structures are now being planned or constructed for waters of 900 feet or more in depth. Though such platforms remain in many instances the most practical way of recovering hydrocarbons from such depths, such great depths and turbulent environmental conditions combine to push the technology of platform construction to approach the state of the art of the metallurgy and designs involved.

Many other examples are evident of solid structural members subject to stress being critical to operation, safety, and the like. For example, weld joints joining hull plates on tankers and the like are critical. For example, if a member holding a helicopter blade, certain aircraft members, a highly stressed crane member, a bridge member, a reactor member, a pressure vessel, or the like fails due to stress cracking, the results can be catastrophic loss of human life and equipment as well as loss of productivity.

One possible failure site of great importance is the heat affected zone adjacent to a weld joining a structural member of an offshore platform to another member of the platform, particularly when the joint and member are critical to the integrity of the structure and subject to stress. If such structural members were to fail, the entire platform might be in danger with possible loss of life, environmental damage, and hundreds of millions of dollars loss of investment and loss production.

Therefore, it is extremely important that any cracks forming in such structural members be detected at the earliest possible stage so that appropriate repairs can be made, or if immediate repairs are impossible due to a storm, that personnel can be evacuated and operations shut in.

Various attempts have been made to detect such cracks. For example, visual inspection has been employed. Such visual inspection can be greatly enhanced by applying a material to the member, removing the material from the surface, and then applying a second material which reacts with the first to form a dye so that the first material oozing from a crack causes the crack to stand out to visual inspection. This method is commonly known as the dye-check method. However, this method is often not practical. Particularly, in the case of weld joints which are under water, it is not feasible for obvious reasons.

Accoustic emission methods have also been employed. However, a major disadvantage of such methods is that the equipment is relatively complex, and it is also difficult, if not impossible, using such equipment to determine the extent or site of the crack, or to determine small cracks in critical members at an early stage.

A third method which has been employed is the magnetic particle orientation method which is useful with ferrous metals. However, this method is also not practical for application to underwater joints and in a number of other situations.

Ultra-sonic tests have also been employed. However, these methods are generally geometry dependent. Such methods are also highly surface condition dependent, that is, the surface must be relatively smooth in order to use such ultra-sonic methods.

U.S Pat. No. 3,667,862 discloses detecting a crack in a wall of a hollow object, exemplarily a blade spar of a rotor blade for a helicopter, by pulling a vacuum on the inside of the hollow body and sensing loss of vacuum. However, this method is not suitable for detection of cracks in non-permeable, solid structural members. It also fails to detect a crack until the crack has completely penetrated the hollow body which is sensed.

Other methods of detecting cracks are known but lack suitability for early detection of cracks or are not otherwise suitable for application to the problem outlined above.

In another art, U.S Pat. Nos. 3,949,596, 2,660,053, 1,371,484, 3,524,342, 4,002,055, and 3,043,129 are exemplary of references showing detection of leaks in vessels by forming a sealed cavity over a possible leak site such as a joint or the like and then pulling a vacuum on the cavity to detect a leak by loss of vacuum, by soap bubbles, or by a tracer gas placed within the vessel. Such methods are not suitable for solution of the problems outlined heretofore for a variety of reasons. Principally, such methods relate to detection of leaks in closed vessels not to detection of formation of cracks in structural members. They also relate to detection of pre-existing leaks, not to detection of cracks formed from environment conditions during a monitoring period.

Our invention constitutes a substantial advance in the art by providing for early detection of cracks in non-permeable, solid structural members subject to stress at an early enough stage that corrective action can be taken. In doing so, it solves a major problem in the art of offshore oil production and a number of other enterprises.

OBJECTS OF THE INVENTION

An object of the invention is to provide a process for early detection of cracks in non-permeable, structural members subject to stress before the cracks traverse the member.

Another object of the invention is to provide an apparatus for early detection of cracks in non-permeable, structural members subject to stress before the cracks traverse the member.

SUMMARY OF THE INVENTION

A process and apparatus are provided for the early detecting of the formation of a crack in a nonpermeable, structural member subject to stress before the crack traverses the member, wherein the process comprises:

(a) forming a cavity in the structural member or adjacent thereto such that a crack forming in the structural member provides a passage for the fluid to flow between the environment and the cavity without passing through the entire structural member,
(b) sealing a fluid passageway in fluid communication from the cavity to a source of pressure different than ambient pressure at the structural member,
(c) imparting a higher or lower pressure to the cavity and the fluid passageway, than ambient, and,
(d) monitoring the internal pressure in the cavity and fluid passageway with the pressure sensor, such that a crack in the structural member penetrating to the cavity allows passage of fluid between the environment and the cavity and is thus detected by the vacuum sensor.

Thus, in one aspect, vacuum loss in the cavity is employed to detect a crack. Thus, in another aspect early detection of any cracks at critical sites on an offshore platform is effected.

DESCRIPTION OF THE DRAWINGS

Figure 1:
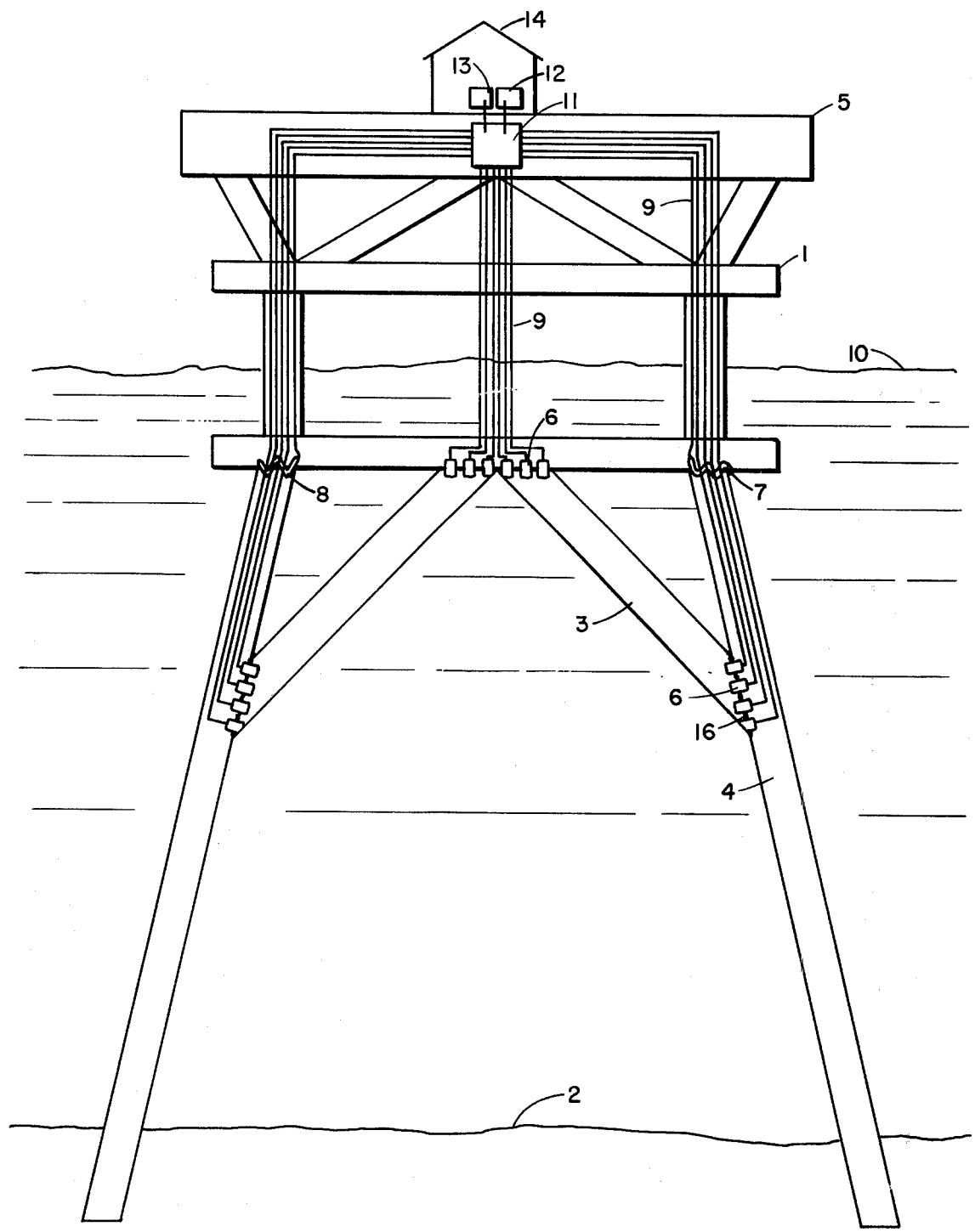
FIG. 1 is a schematic cross section of an offshore platform having an example of the apparatus of the invention aboard for monitoring stressed members.

FIG. 1 illustrates a cross section of an offshore platform having the apparatus of this invention implaced thereon.

The platform 1 rests upon and is affixed to sea floor 2 with its major portion submerged below the water level 10. It is comprised of various members including deck member 5, bracing member 3, and leg member 4. The members are joined together to form the platform by welds 16 as in the joint between member 3 and member 4. Patches 6 of the invention are connected by vacuum lines 9 to a central manifold and controller 11 and also in fluid communication with vacuum source 12. Exemplary serpentine configuration patch 7 and zig-zag configuration patch 8 are also employed to monitor the heat affected zone adjacent to weld joints joining other critical members which are stressed by wave action. Vacuum manifold and controller 11 is connected to readout 13 which combination has the capability of sequentially monitoring the patches and providing an alarm of leakage beneath any patch by loss of vacuum in the line associated therewith. These components are sheltered by shelter 14 on the platform.

Figure 2:
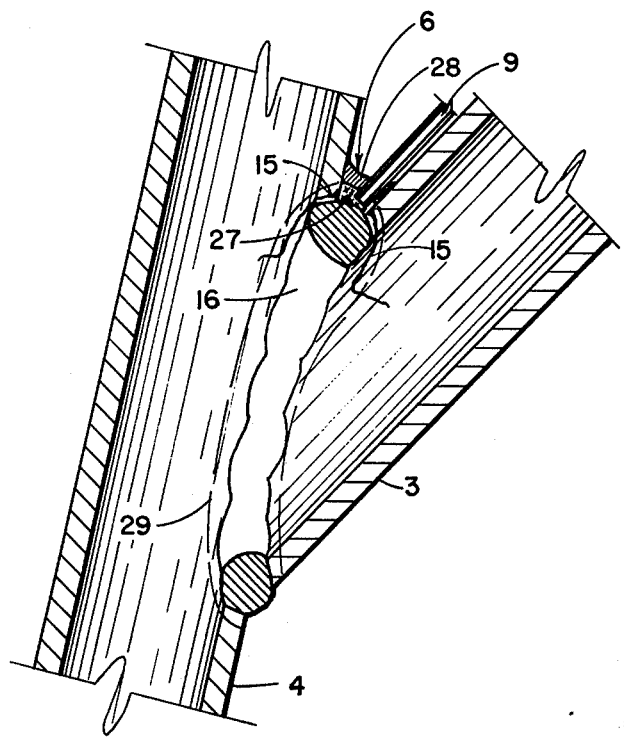
FIG. 2 illustrates a cross sectional view of a patch situated to monitor a weld joint and associated heat affected zone where one member of the platform is joined to another member of the platform.

FIG. 2 illustrates a cross section of bracing member 3 joined to upright member 4 by a weld 16 having a heat affected zone 29 immediately adjacent on each side. Vacuum line 9 is sealed in fluid communication within the patch 6 and through permeable material 27 to the heat affected zone 29 subject to cracks 15 by impermeable sealant 28.

Figure 3:
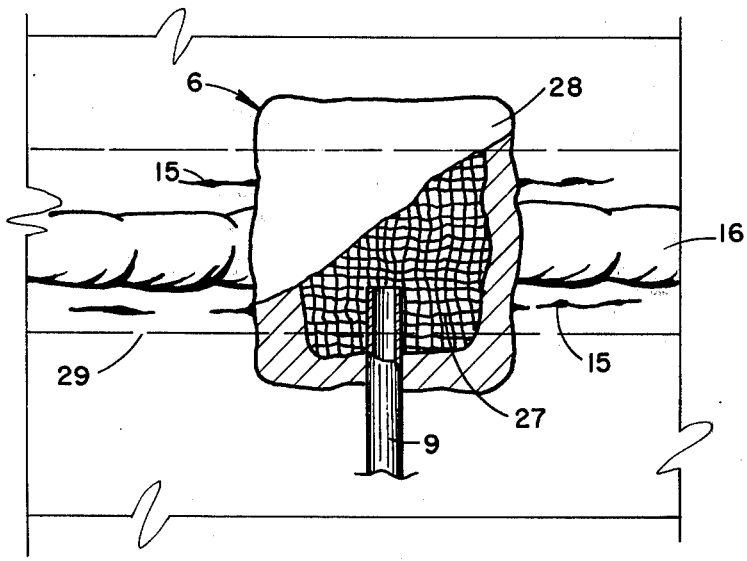
FIG. 3 illustrates a top sectional view of a patch situated on a weld and heat affected zone joining one member of the platform to another.

FIG. 3 illustrates a top sectional view of a patch similar to that shown in FIG. 2. Vacuum line 9 is in fluid communication with a portion of the heat affected zone 29 adjacent to weld 16 subject to cracks 15 by way of permeable material 27 within patch 6 sealed from the environment by impermeable sealant 28 but for any passageway formed by cracks 15.

Figure 4:
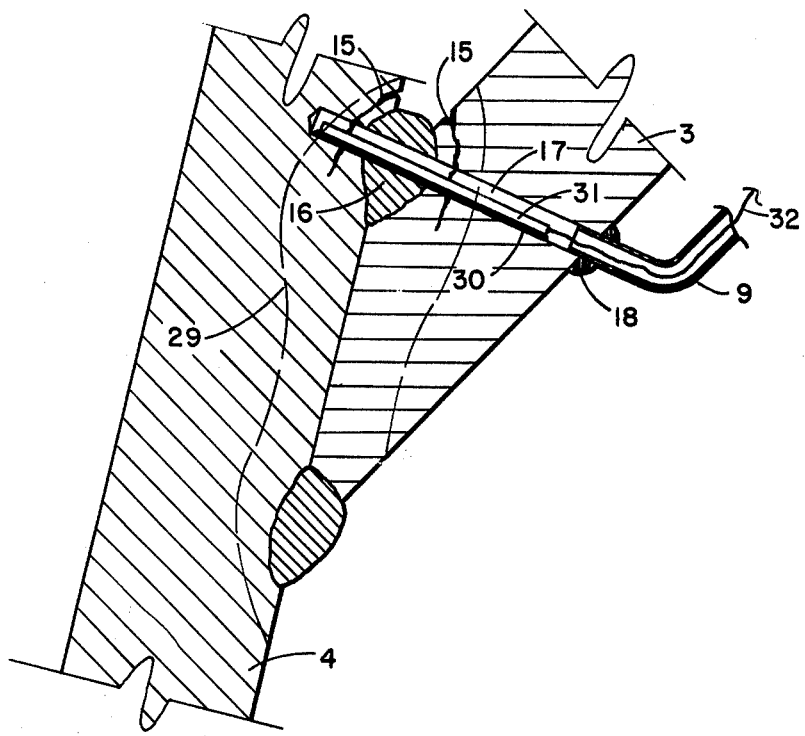
FIG. 4 shows a cross sectional view of an embodiment wherein a cavity is formed into the heat affected zone near a weld joint on the platform. It further shows the embodiment wherein a strain gauge is mounted in the cavity.

FIG. 4 illustrates another embodiment by a cross sectional view. Vacuum line 9 is sealed by sealant 18 to a cavity 17 milled through the weld 16 and heat affected zone 29 joining member 3 to member 4. A strain gage 31 is adhered to the side of the cavity 17 by adhesive 30 and connected to a read-out (not shown) by an insulated conductor 32 situated within vacuum line 9.

Any cracks 15 penetrating the heat affected zone 29 to the cavity 17 result in entrance from the environment of water (a fluid which is immediately detected by a decrease in the vacuum and a triggering of an alarm as shown in FIG. 1).

Figure 5:
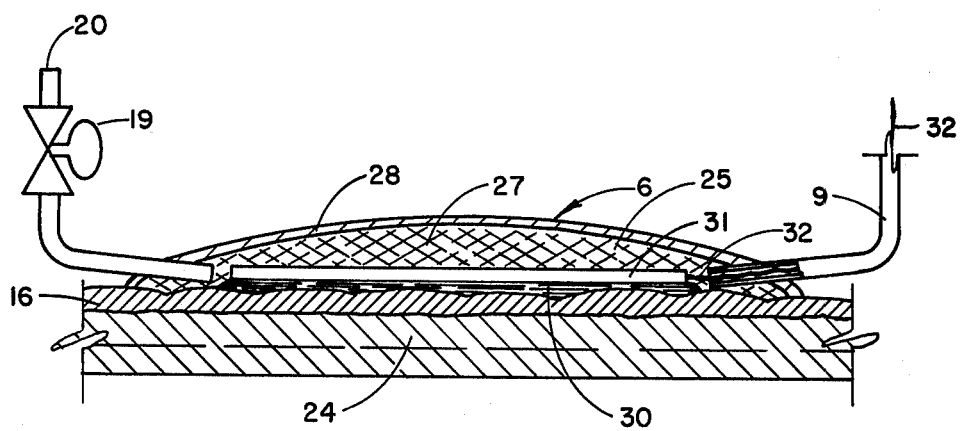
FIG. 5 shows a cross sectional view of an embodiment wherein provision is made to flush fluids through a patch embodiment of the invention and wherein a strain gauge is mounted in the patch.

FIG. 5 illustrates yet another embodiment by a vertical cross sectional view. A strain gage 31 is adhered to within the vicinity of weld 16 by means of adhesive 30. It is connected to a read-out (not shown) by an insulated conductor 32 situated within vacuum line 9 which pulls a vacuum of patch 6 comprising permeable material 27 forming a continuous fluid permeable cavity 25 sealed from the environment by the impermeable sealant 28. The cavity 25 is sealed by sealant 28 on the opposite end to flushing tube 20 and valve 19 by which cavity 25 containing permeable material 27 and the system can be flushed.

Figure 6:
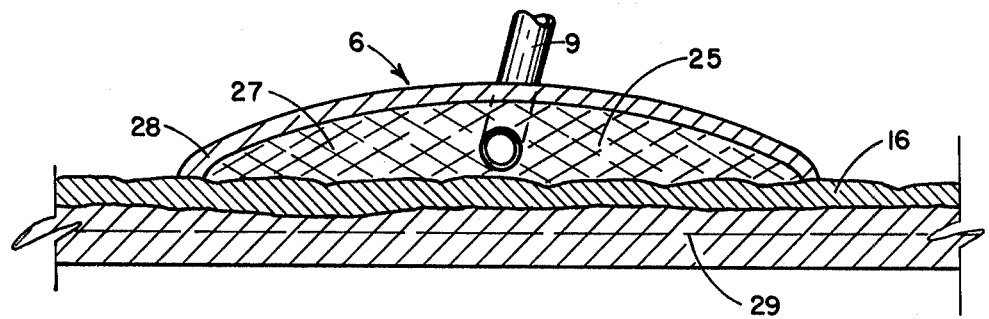
FIG. 6 illustrates a cross sectional view of an embodiment of the invention wherein a patch comprising a sealant overlaying a permeable material monitoring a heat affected zone adjacent to a weld joint is employed.

FIG. 6 illustrates by another cross sectional view an embodiment wherein vacuum line 9 is sealed to cavity 25 comprising a permeable material 27 by sealant 28 to form patch 6 covering a portion of weld 16 and heat affected zone 29.

Figure 7:
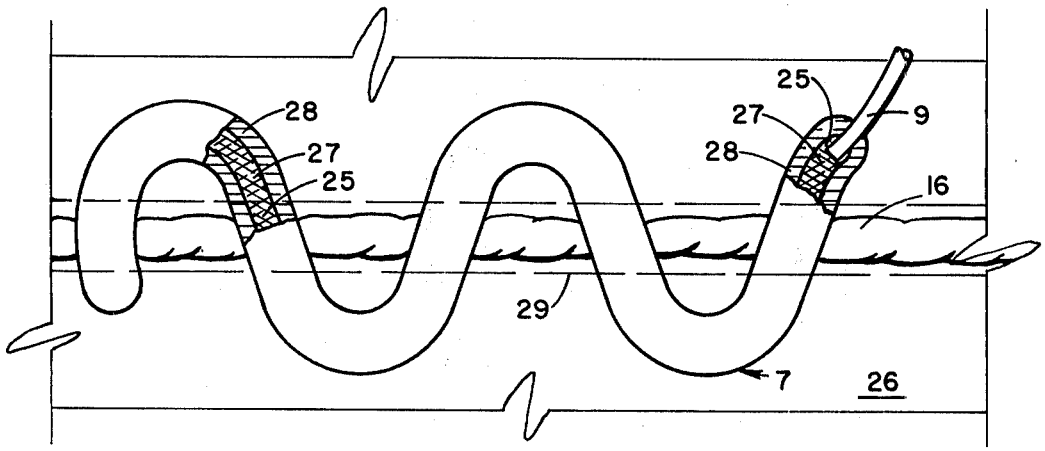
FIG. 7 illustrates a patch embodiment having a serpentine configuration monitoring a weld joint and the heat affected zone associated therewith.

FIG. 7 illustrates an embodiment wherein the patch 7 has a serpentine configuration wherein vacuum line 9 is sealed to cavity 25 comprising permeable material 27 by impermeable sealant 28 and wherein the serpentine configuration patch criss-crosses weld 16 and heat affected zone 29 on substrate 26.

Figure 8:
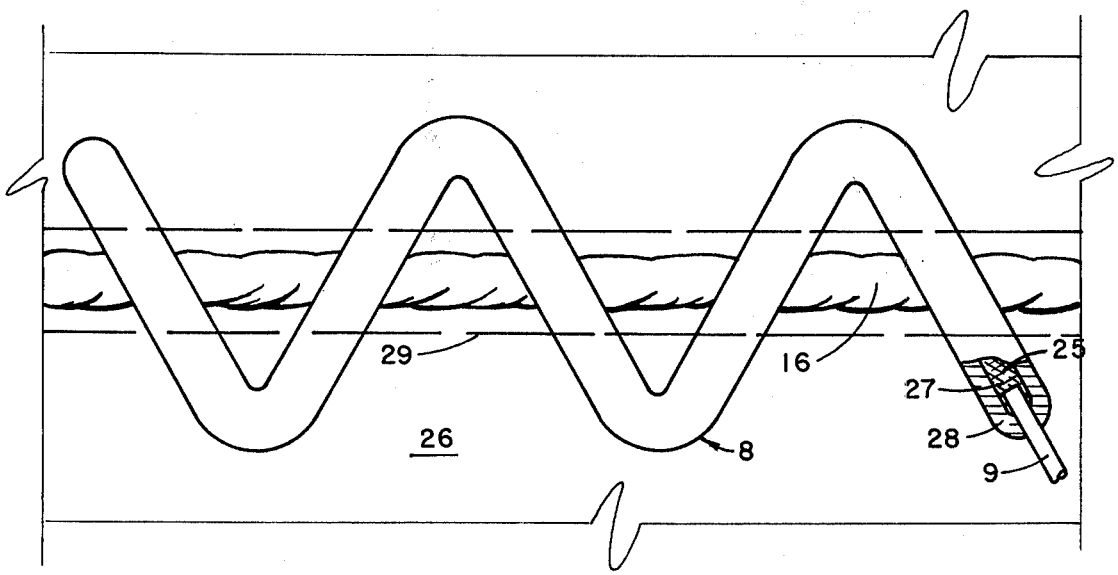
FIG. 8 illustrates a zig-zag configuration of a patch embodiment wherein a weld joint and the heat affected zone are monitored for cracks.

FIG. 8 illustrates another embodiment wherein patch 8 has a zig-zag configuration and comprising vacuum line 9 as sealed to cavity 25 formed by permeable material 27 and sealed from the environment by impermeable sealant 28. The patch having zig-zag configuration covers weld 16 and heat affected zone 29 on substrate 26.

Figure 9:
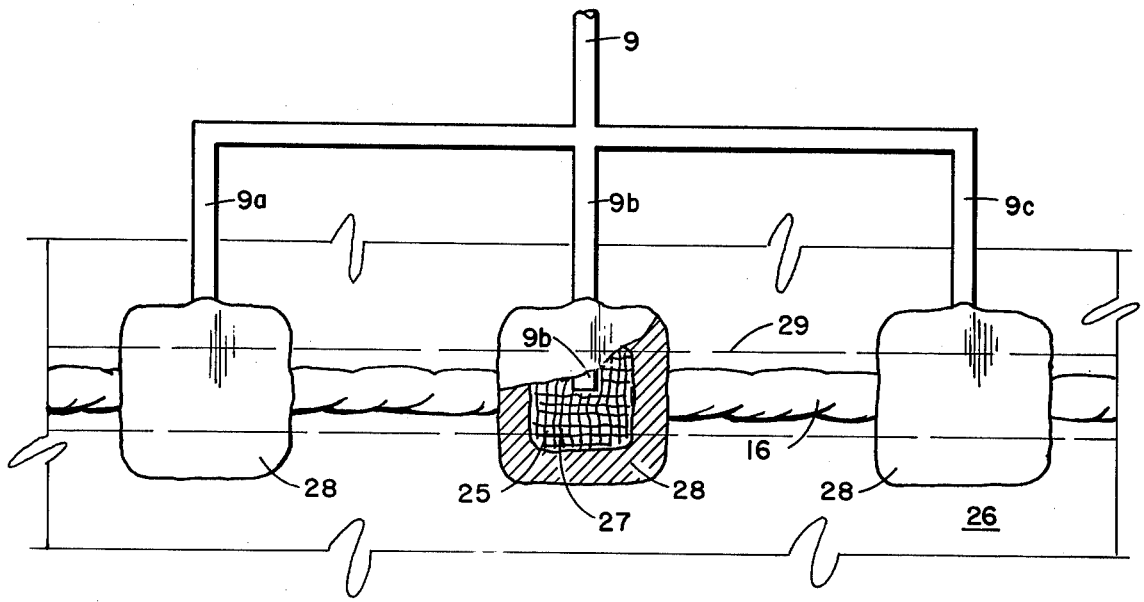
FIG. 9 illustrates an embodiment wherein a series of patches are employed to monitor a weld joint and a heat affected zone with the vacuum lines manifolded.

FIG. 9 illustrates by top view section another embodiment wherein a plurality of patches are employed to monitor weld 16 and heat affected zone 29 on substrate 26. Patches comprising permeable material 27 in cavities situated over the heat affected zone and weld 16 are sealed from the environment by impermeable sealant 28 and are joined through a manifold and lines 9A, 9B, and 9C and thence through vacuum line 9 to the system.

Figure 10:
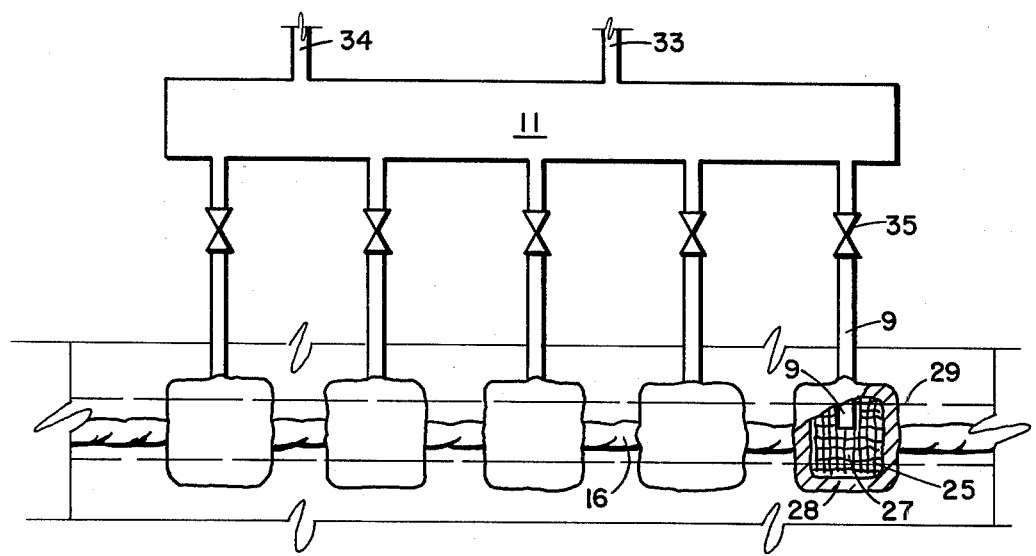
FIG. 10 is a schematic illustration of an embodiment wherein a series of patches are monitored.

FIG. 10 schematically illustrates yet another embodiment wherein patches over substrate having the same numbering system and configuration as shown in the previous figures are joined by lines 9 to manifold 11. Line 34 connects to a vacuum source and valves 35 are sequentially switched and the pressure in each of lines 9 is determined to pinpoint on a read-out with alarm which of the patches is indicating loss of vacuum and consequently the probability of early crack formation.

Figure 11:
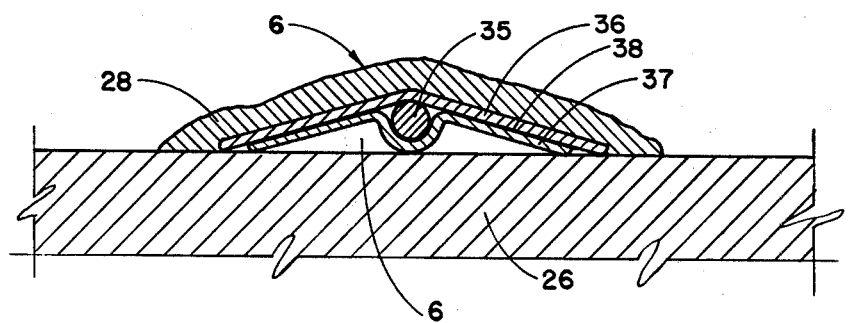
FIG. 11 is a cross section view of another patch embodiment of the invention wherein a wire member extends from the vacuum line and props up a foil sheet.

FIG. 11 shows a cross section of a patch embodiment of the invention wherein a wire member extends from the vacuum line at a point away from the vacuum line. Thus wire member 35 props up an upper foil sheet 36 which passes over the wire member and is held in association therewith by lower foil sheet 37 which is adhered to upper foil sheet 36 with an adhesive 38 at the interface therebetween. The foil sheets are sealed from the environment and to substrate 26 by sealant 28 to form cavity 25 for fluid communication to vacuum line 9 (not shown).

PREFERRED EMBODIMENTS OF THE INVENTION

According to our invention, a cavity is provided in the structural member or adjacent thereto such that a crack forming in the structural member provides a passage for a fluid to flow between the environment and the cavity without passing through the entire structural member, a fluid passageway is sealed in fluid communication from the cavity to a lower or higher pressure source and to a pressure sensor, a pressure different than ambient at the member is applied to the cavity and the fluid passageway, and the internal pressure is monitored in the cavity and fluid passageway with the pressure sensor, so that a crack in the structural member penetrating to the cavity allows passage of fluid to or from the environment and is thus detected by the pressure sensor.

In a preferred embodiment the pressure imparted to the cavity is a very low pressure or a vacuum. The vacuum employed can be in the millitorr range for most applications. Devices to measure these low pressures (vacuum) are very sensitive, reliable, and relatively inexpensive.

If the crack detector is located under water, the fluid which will lower the vacuum will be water vapor. Thus, the triple point of water is 0.0076° C. at 0.46 torr. therefore, all water above freezing and below 0.46 torr will be subject to the gas laws:

$$\frac{P_1 V_1}{T_1} = \frac{P_2 V_2}{T_2}$$

Thus, one mole of water as a gas (18 grams) would fill a volume of 22.4 liter. at 273° K. and 760 torr. Dropping the pressure to convert the water to a gas will give 18 grams equal 22.4 $\times$ 10$^4$ liters $\times$ 760 $\times$ 10$^{-4}$ torr. Therefore, a crack detection system of 22.4 liters volume maintained at 7.6 $\times$ 10$^{-4}$ torr which is an easily maintained vacuum would result in a water leak of 0.0018 grams (ml) (approximately 1/25th of a water drop from an eyedropper) leaking into the system raising the pressure by 7.6 $\times$ 10$^{-2}$ torr for a total pressure of 0.07676 torr. This constitutes a pressure increase of about 100 times and is readily detectable. Therefore, it is seen that even very minute leaks under the patches or into the cavities of water or of another fluid such as air result in considerable loss of vacuum and are readily detectable by the sensor devices available.

A crack propagating on a heat affected zone intersected with a patch will provide a leak path from the exterior to the interior of the patch when the patch embodiment is employed. This leak is readily detected by the pressure sensor in fluid communication with that patch.

According to one presently preferred embodiment, the vacuum line from a patch, or from a series of patches manifolded together and covering a weld joint and heat affected zone associated therewith can have a vacuum pulled by the vacuum source. Thereupon, the line can be shunted by a suitable valve arrangement to a differential pressure transducer such as described in U.S. Pat. No. 3,505,634, or more preferably a thermocouple gauge. Thereupon if vacuum is lost in the line between the transducer and the patch due to crack propagation, the transducer provides an electrical signal indicating the pressure difference. This can be rigged to trigger an alarm such as a light, bell, or the like. An indicating board having a series of alarm devices can be set up to monitor critical points on the entire platform. When a series of patches are placed across a critical weld and heat affected zones associated therewith, positive response of patches in a row in a progression indicates extreme probability that the joint is failing. The transducer or thermocouple guage also can produce an electrical signal proportional to the differential in pressure, and a preset amount of the signal can be designed into the system so that an alarm will only be triggered when this pre-arranged difference in pressure is reached. Alternatively, a sensor and ion pump can be provided for each patch. Alternatively, one or more differential pressure transducers or thermocouple guages can be employed with sequential scanning of the various lines between the pressure source and the patches through the transducer, or thermocouple guage by a series of valves and solenoids.

According to another particularly preferred embodiment the vacuum line from each patch is run to a vacuum manifold which is evacuated with a conventional mechanical vacuum pump employing cold traps absorbants and the like. High vacuum is obtained with an ion pump. A thermocouple guage is positioned in each line between the patch and manifold. Upon penetration of the patch by a crack, fluid enters and the differential pressure is detected by the thermocouple guage which triggers an alarm and activates a solenoid activated valve situated in the vacuum line between the thermocouple guage and the vacuum manifold. Advantage of this arrangement are that each individual patch line is monitored and high vacuum is not lost in the system upon a single patch losing vacuum. The time and trouble needed to isolate the open line and rebuild vacuum first with a conventional pump and then the ion pump is thus avoided. Also the system is not contaminated with the fluid leaking in and a hiatus in monitoring is avoided. This embodiment is of particular value when a large number of sites on an offshore platform are monitored.

The vacuum or higher pressure source employed can be any conventional device for producing vacuum or pressure. Thus, a conventional vacuum pump can be employed to reduce pressure to a low level. Suitable absorbants, cold traps, and the like can be employed. High vacuum can readily be provided with suitable ion pumps which are readily available.

In one embodiment for use upon an offshore platform, the pumping system is fabricated to handle up to 100 detectors and to produce a pressure drop of about 2.5 liters per second at $10^{-5}$ torr for the first day with steadily declining pressure for several days to about $10^{-7}$ torr. The vacuum system, of course, can be designed for the particular monitoring system employed, and this is well within the skill of engineers skilled in the art, or can be readily determined by simple experimentation. The vacuum and monitoring system can be fabricated largely of conventional off-the-shelf hardware. Considerable variety of such hardware is available from a number of sources, exemplarily, the Varian Company.

The sealant employed according to this invention can be any of a number of sealants. For example, solder, brazing material, epoxy-based sealants, silicone materials, butyl rubber sealants, hot melt formulations, and any of a variety of other materials can be employed if desired. According to a presently preferred mode, a very suitable and versatile material which has been found to be very satisfactory is KNEDATITE sealant available from Knedatite Division of Polymeric Systems, Inc., 860 Cross Street, Potstown, PA. It is an epoxy/polyamide system which is supplied as a two-part, hand-mixable tape which is then kneaded together, and cures within a few hours. This epoxy-based sealant is easily formed into the covering for a patch within one hour after mixing and cures into a flexible, tough, hard, well-adhering material. It can be applied under water and has been found to make quite suitable bonds in its use as a sealant as described according to this invention. It has been satisfactorily tested on V-bend fatique samples both in air and under water with complete success.

A patch fabricated with this epoxy-based material has been tested at pressure up to 500 psig in water and found to have good vacuum integrity without loss of imperviousness.

The permeable material 27 or bleeder materials which can be implaced in the cavities of this invention particularly in the embodiment wherein patches are employed, can be any material which will hold the cavity open to the flow of fluid when vacuum is applied. Suitable materials can include paper, cloth prepared of natural or synthetic fibers, open-cell foamed plastics, and the like. A fabric woven of Dacron fibers is quite suitable.

Alternatively the patch can have a wire member or the like extending from the end of the vacuum line which props up a foil sheet or similar cover to hold open a vacuum passage under the sealant of the patch.

According to a presently preferred mode of operation, when patches are employed, the porous material, or bleeder material is overlain with an impermeable barrier before the sealant is applied in fabricating the patches. The barrier material can be any of a number of substances which are impermeable to fluids. For example, thin metal foil, such as aluminum foil, polyester terephthalate plastic films, of which a commercially available example is trademarked MYLAR film, are quite suitable.

In the embodiment wherein a strain guage is implaced within the cavity formed by the patch or in the cavity milled into the structural member, the strain guage can be adhered by any suitable adhesive. Examples include commercially available epoxy resins, silicone-based adhesives, cyanoacrylatebased adhesives, and the like.

The strain guage within the patch or cavity embodiment is very advantageous in that assurance is provided by vacuum integrity that the strain guage sensor is protected from the environment and is not being affected by moisture and the like. Data obtained from the combination is valuable for correlation purposes.

Though the invention has been described in terms of vacuum, that is, very low pressure, in many places, it should be understood that pressure above ambient at the patch or cavity sites can also be employed. Any suitable fluid, preferably air, or an inert gas can be employed for this positive pressure embodiment. However, if positive rather than negative pressure (vacuum), as relating to ambient pressure, is employed, care must be taken not to exceed the pressure containable by the sealants and lines employed.

It is an important aspect of our invention that the portion of the structural member to be monitored not be entirely sealed from the environment with the sealant. Otherwise cracks can propagate under the sealant and not be detected until they penetrate through the member. Coverage of less than 10% of the surface is often quite suitable.

The foregoing exemplification and description are provided to more fully explain the invention and provide information to those skilled in the art on how to carry it out. However, it is to be understood that such is not to function as limitation on the invention as described and claimed in the entirety of this application.

We claim:

1. A process for the early detecting of the formation of a crack in a non-permeable, structural member subject to stress before the crack traverses the member, the process comprising:
   (a) forming a cavity in the structural member or adjacent thereto such that a crack forming in the structural member provides a passage for a fluid to flow between the environment and the cavity without traversing the structural member,
   (b) sealing a fluid passageway in fluid communication from the cavity to a source of pressure different than ambient at the structural member and to a pressure sensor,
   (c) imparting a higher or lower pressure than ambient to the cavity and the fluid passageway, and,
   (d) monitoring the internal pressure in the cavity and fluid passageway with the pressure sensor, such that a crack in the structural member penetrating to the cavity allows passage of fluid between the environment and the cavity and is thus detected by the pressure sensor.

2. The process of claim 1 wherein the cavity is milled into the heat affected zone adjacent to a weld joint on the structural member and the pressure imparted to the cavity in (c) is a vacuum.

3. The process of claim 2 wherein a plurality of cavities are formed in the heat affected zone.

4. The process of claim 2 wherein the structural member is a part of an offshore platform and wherein the heat affected zone is adjacent to a weld joint joining the member to another member of the offshore platform.

5. The process of claim 4 wherein the passageway is a metal tube, wherein the cavity is a drill bore having a volume less than 1% of the heat affected zone, wherein the drill bore traverses a substantial portion of the heat affected zone and has a length at least 10 times its diameter, wherein the sealant is an epoxy resin based sealant, wherein the heat affected zone sensed is below the surface of the water, and wherein the pressure sensor is above the surface of the water.

6. The process of claim 5 wherein the sensor triggers an alarm upon loss of vacuum in the system.

7. The process of claim 5 wherein a plurality of cavities are formed in a heat affected zone near a weld joint on a critical stressed member.

8. The process of claim 7 wherein a plurality of structural members are monitored with a common vacuum passageway and vacuum source, wherein loss of vacuum in a line going to any cavity results in triggering of an alarm and shutting off that line from the common vacuum passageway.

9. The process of claim 1 wherein the fluid passageway comprises a tubular member and the cavity is formed adjacent to the structural member by adhering the tubular member to the structural member with a sealant.

10. The process of claim 1 wherein the fluid passageway comprises a tubular member, wherein the cavity is formed adjacent to the structural member by forming a patch by placing the tubular member adjacent to the structural member in fluid communication with a permeable material also placed adjacent to the structural member and sealing both from the environment with an impermeable sealant, and wherein the pressure imparted to the cavity in (c) is below ambient or a vacuum.

11. The process of claim 10 wherein the tubular member is overlain by the permeable material, the permeable material is overlain by an impermeable barrier, and both are sealed from the environment by the impermeable sealant.

12. The process of claim 10 wherein the tubular member is underlain by the permeable material, the tubular member is overlain by an impermeable barrier, and both are sealed from the environment by the impermeable sealant.

13. The process of claim 10 wherein the structural member is a part of an offshore platform and is secured to other structural members by weld joints, wherein the patch is placed across a portion of the heat affected zone adjacent to a weld joint joining the member to another member of an offshore platform.

14. The process of claim 13 wherein the patch covers no more than 50% of the heat affected zone, wherein the sealant is an epoxy resin based sealant, wherein the heat affected zone sensed is below the surface of the water, and wherein the pressure sensor is above the surface of the water.

15. The process of claim 14 wherein the pressure sensor triggers an alarm upon loss of vacuum in the system.

16. The process of claim 15 wherein a plurality of patches are placed across a heat affected zone near a weld joint on a critical stressed member.

17. The process of claim 16 wherein a plurality of structural members are monitored with a common vacuum passageway, wherein an alarm is triggered by the sensor upon a pre-determined loss of vacuum, and wherein the line having leakage is shut off.

18. The process of claim 17 wherein the tubular member in the patch is underlain by the permeable material, and overlain by an impermeable barrier, and both are sealed from the environment by the impermeable sealant.

19. The process of claim 10 wherein strain on the structural member is monitored by adhering a strain guage sensor to the structural member within the patch and passing an insulated electrical conductor therefrom to a read-out therefore.

20. The process of claim 19 wherein the structural member is a part of an offshore platform, wherein the patch is placed across the heat affected zone adjacent to a weld joint on the structural member, wherein the heat affected zone is adjacent to a weld joint joining the member to another member of the offshore platform, wherein the passageway is a metal tube, wherein the heat affected zone sensed is below the surface of the water, wherein the vacuum sensor is above the surface of the water, and wherein the insulated electrical conductor is passed through the metal tube for at least the distance to above the surface of the water.

21. An apparatus for the early detecting of a crack in a non-permeable, structural member subject to stress before the crack traverses the member, the apparatus comprising:
(a) a cavity formed from the surface into the structural member,
(b) a fluid passageway sealed to and passing from the cavity to a source of pressure different than ambient and to a sensor providing fluid-tight communication therebetween.

22. The apparatus of claim 21 wherein a strain guage sensor is adhered to the structural member within the cavity and wherein an insulated conductor passes from the strain guage sensor to a read-out device therefore.

23. The apparatus of claim 22 wherein the cavity is milled into the heat affected zone adjacent to a weld joint on the structural member, wherein the source of pressure in (b) is a vacuum source, wherein the structural member is a part of an offshore platform, wherein the heat affected zone is adjacent to a weld joint joining the member to another member of the offshore platform, wherein the passageway is a metal tube, wherein the cavity is a drill bore having a volume less than 1% of the heat affected zone, wherein the drill bore traverses a substantial portion of the heat affected zone, wherein the sealant is an epoxy resin based sealant, wherein the heat affected zone sensed is below the surface of the water, wherein the pressure sensor is above the surface of the water, wherein the conductor from the strain guage to the read-out is passed through the vacuum passageway to at least above the surface of the water.

24. The apparatus of claim 23 wherein the sensor is rigged to trigger an alarm upon loss of vacuum in the system, wherein a plurality of structural members are monitored with a common vacuum passageway, and wherein an alarm is rigged to be triggered by the pressure sensor upon a pre-determined loss of vacuum.

25. An apparatus for the early detecting of a crack in a non-permeable, structural member subject to stress before the crack traverses the member, the apparatus comprising:
(a) a fluid-tight passageway in sealed vacuum communication between a source, of pressure different than ambient, a pressure sensor, and the surface of the structural member,
(b) a permeable material adjacent to the structural member and the fluidtight passageway and in fluid communication therethrough to both,
(c) an impermeable sealant covering the end of the passageway and the permeable material providing a fluidtight seal between them and the environment.

26. The apparatus of claim 25 wherein the fluid-tight passageway is a vacuum passageway, one end of the vacuum passageway is overlain by the permeable material, the permeable material is overlain by an impermeable barrier, and both are sealed from the environment by the impermeable sealant.

27. The apparatus of claim 26 wherein the sealant covers no more than 10% of the surface of the structural member to be sensed.

28. An apparatus for the early detecting of a crack in a non-permeable, structural member subject to stress before the crack traverses the member, the apparatus comprising:
(a) a source of pressure different than ambient,
(b) a pressure sensor,
(c) a fluid-tight line connecting the non-ambient pressure source and the pressure sensor,
(d) a patch sealed in fluid-tight relationship to the line, the patch comprising a permeable material adjacent to the end of the line and to the structural member and sealed thereto with a fluid impermeable sealant.

29. The apparatus of claim 28 wherein the patch is placed across the heat-affected zone adjacent to a weld joint on the structural member, wherein the source of pressure other than ambient is a vacuum source, wherein the pressure sensor is a vacuum sensor, and wherein the fluid-tight line is a vacuum-tight line.

30. The apparatus of claim 29 wherein a plurality of patches are placed across the heat affected zone.

31. The apparatus of claim 29 wherein the structural member is a part of an offshore platform and wherein the heat affected zone is adjacent to a weld joint joining the member to another member of the offshore platform.

32. The apparatus of claim 29 wherein the patch is elongated and is placed to cover in a zig-zag or serpentine fashion a substantial portion of the heat affected zone adjacent to a weld joint joining an underwater member of an offshore platform to another underwater member of an offshore platform.

33. The apparatus of claim 29 wherein the sensor is rigged to trigger an alarm upon loss of vacuum in the system.

34. The apparatus of claim 33 wherein a plurality of patches are monitored with a common vacuum passageway and wherein an alarm is triggered by the sensor upon a pre-determined loss of vacuum.

35. The apparatus of claim 34 wherein substantially all critical stressed weld joints on an offshore platform are monitored.

36. the apparatus of claim 35 wherein the patches comprise a first layer of porous paper; overlying the paper, the end of the vacuum line; overlying the end of the vacuum line, a layer of metallic foil covering the end of the vacuum line and the porous paper; overlying the foregoing, an overlying layer of epoxy-based sealant forming a fluid-tight barrier adhering the paper, the end of the vacuum line, and the foil barrier to the structural member.

37. The apparatus of claim 28 wherein the patches have an opening opposite the end of the line such that the system can be flushed with a fluid.

38. The apparatus of claim 37 wherein the patch has a length at least 2 times its width.

39. The apparatus of claim 29 wherein a plurality of patches are placed across the heat affected zone adjacent to a weld joint on the structural member, wherein the structural member is part of an offshore platform and wherein the heat affected zone is adjacent to a weld joint joining the member to another member of the offshore platform, wherein the weld joint is under the surface of the water, wherein a common vacuum source, and passageway is employed to pull vacuum on the plurality of patches, wherein a differential pressure sensor is emplaced in fluid-tight relationship in the vacuum line going to each patch, and wherein the differential pressure sensing device in each vacuum line is rigged to trigger an alarm indicating crack penetration within the structural member to admit environmental fluids into the permeable material of that patch.

40. An apparatus for the early detecting of a crack in a non-permeable, structural member subject to stress before the crack traverses the member, the apparatus comprising:
(a) a vacuum source,
(b) a vacuum sensor,
(c) a vacuum tight line connecting the vacuum source and the vacuum sensor,
(d) a patch sealed in vacuum tight relationship to the line, the patch comprising a propping member adjacent to the end of the vacuum line, an impermeable sheet material overlying the propping member so as to form a fluid channel extending therefrom, and the sheet and end of vacuum line sealed from the environment with a fluid impermeable sealant.

41. The apparatus of claim 40 wherein the patch is placed across the heat affected zone adjacent to a weld joint on the structural member.

42. The apparatus of claim 41 wherein a plurality of patches are placed across the weld joint and heat affected zone, wherein the structural member is a part of an offshore platform, wherein the heat affected zone is adjacent to a weld joint joining the member to another member of the offshore platform and is below the water line, wherein a differential pressure sensor is placed in each vacuum line between the vacuum source and each patch, and wherein each differential pressure sensor is rigged to trigger an alarm upon loss of vacuum under the patch effecting a differential pressure.

43. A process for the early detecting of the formation of a crack in a non-permeable, structural member subject to stress before the crack traverses the member, the process comprising:
(a) forming a cavity adjacent to the structural member by forming a patch by placing one end of a tubular member adjacent to the structural member and in fluid communication with a permeable material also placed adjacent to the structural member and sealing both from the environment with an impermeable sealant such that a crack forming in the structural member provides a passage for a fluid to flow between the environment and the cavity without traversing the structural member, (b) sealing the other end of the tubular member in fluid communication to a source of pressure different than ambient at the structural member and to a pressure sensor,
(c) imparting pressure other than ambient to the cavity and the interior of the tubular member, and
(d) monitoring the internal pressure in the cavity and the interior of the tubular member with the pressure sensor; such that a crack in the structural member penetrating to the cavity allows passage of fluid between the environment and the cavity and is thus detected by the pressure sensor.

* * * * *